United States Patent [19]
Wardle et al.

[11] Patent Number: 5,472,534
[45] Date of Patent: Dec. 5, 1995

[54] GAS GENERANT COMPOSITION CONTAINING NON-METALLIC SALTS OF 5-NITROBARBITURIC ACID

[75] Inventors: Robert B. Wardle, Logan; Reed J. Blau, Richmond, both of Utah

[73] Assignee: Thiokol Corporation, Ogden, Utah

[21] Appl. No.: 178,215

[22] Filed: Jan. 6, 1994

[51] Int. Cl.$^6$ .................. C06B 47/08; D03D 23/00
[52] U.S. Cl. .................. 149/36; 149/109.6; 280/741; 544/301
[58] Field of Search .................. 149/36, 109.6; 280/741; 544/301

[56] References Cited

U.S. PATENT DOCUMENTS

| | | | |
|---|---|---|---|
| 3,719,604 | 3/1973 | Prior et al. | 252/186 |
| 4,142,029 | 2/1979 | Illy | 521/95 |
| 4,608,102 | 8/1986 | Krampen et al. | 149/92 |
| 4,948,439 | 8/1990 | Poole et al. | 149/46 |
| 5,015,309 | 5/1991 | Wardle et al. | 149/19.1 |
| 5,035,757 | 7/1991 | Poole | 149/46 |
| 5,084,118 | 1/1992 | Poole | 149/22 |
| 5,139,588 | 8/1992 | Poole | 149/61 |
| 5,197,758 | 3/1993 | Lund et al. | 280/741 |
| 5,428,165 | 6/1995 | Wardle | 544/301 |

OTHER PUBLICATIONS

"Barbituric Acid", J. B. Dickey and A. R. Gray, *Organic Syntheses*, Collective vol. II, p. 60.

"Nitrobarbituric Acid", W. w. Hartman and O. E. Sheppard, *Organic Syntheses*, Collective vol. II, pp. 440–441.

"The Diliturates (5–Nitrobarbiturates) of Some Physiologically Important Bases", C. E. Redemann and Carl Niemann, *Journal of American Chemical Society*, vol. 62, 1990, pp. 590–593.

"New Syntheses of Dilituric Acid", R. Nutiu and I. Sebe, *Chemical Abstracts*, vol. 75, 1971, p. 460.

"New Syntheses of Dilituric Acid", R. Nutiu and I. Sebe, *Rev. Roum. Chim.*, Oct. 26, 1970, vol. 16, pp. 919–923.

"Azione Dell'HCI Gasoso Sull'etere Nitro–Cianacetico In Soluzione Alcoolica", *Gazz. Chim. Ital.*, vol. 42, pp. 223–224.

"The Nitration Of 4–Methoxy– And 4–Ethoxy Benzophenone", J. Van Alphen, *Recviel Trav. Chem. Pay–Bas.*, vol. 8, pp. 381–382 (1930).

"Contributions a la Connaissance de L'action de L'acide Azotique sur les Corps Organiques", MM. A. P. N. Franchimont and E. A. Klobbie, *Recviel Trav. Chem. Pay–Bas.*, vol. 49, pp. 283–306.

"Darstellug von Barbitursäure und N–Alkyl–barbitursäuren", Heinrich Biltz und Herbert Wittek, *Ber.* vol. 54, pp. 1035–1058 (1921).

*Primary Examiner*—Peter A. Nelson
*Attorney, Agent, or Firm*—Madson & Metcalf; Ronald L. Lyons

[57] ABSTRACT

A composition is provided which comprises a fuel effective amount of a heterocyclic compound represented by the formula:

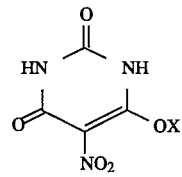

wherein X is a non-metallic cation; and an oxidizing effective amount of an inorganic oxidizer. The oxidizer can be an inorganic nitrite, an inorganic nitrate, a metal peroxide, a metal oxide, a metal hydroxide, an inorganic perchlorate, or an inorganic chlorate. A binder can be added, if desired. An automotive air bag inflator and a method for generating gas are also disclosed.

18 Claims, No Drawings

GAS GENERANT COMPOSITION CONTAINING NON-METALLIC SALTS OF 5-NITROBARBITURIC ACID

FIELD OF THE INVENTION

The present invention concerns pyrotechnic compositions, and in particular gas generant compositions, containing non-azide fuels comprising non-metallic salts of 5-nitrobarbituric acid.

BACKGROUND OF THE INVENTION

There have been a number of proposed non-azide gas generant compositions.

Among those is a composition based on a very restricted number of metallic salts of 5-nitrobarbituric acid and an equally restricted number of metal-cation containing oxidizers which is described in U.S. Pat. No. 5,015,309, the disclosure of which is incorporated herein by reference. According to the known proposal, a non-azide gas generant is composed of about 25 to 75% by weight of anhydrous metal salts of 5-nitrobarbituric acid wherein the metal is selected from metals of Group I-A of the Periodic Table of Elements (except sodium), calcium, strontium, or barium, and about 75 to 25% by weight of an anhydrous oxidizing salt having a metal cation selected from the group consisting of metals of Group I-A of the Periodic Table of Elements (except sodium), calcium, strontium, or barium, plus from 0 to 5% by weight of a binder. Although these gas generant compositions have received some interest, the compositions suffer from various drawbacks. Of the most promising compositions is one containing the potassium salt of 5-nitrobarbituric acid. However, compositions based on the potassium salt exhibit several severely limiting drawbacks such as high particulate levels and very high carbon dioxide levels. Solids from the combustion of the preferred potassium salt include potassium hydroxide and potassium oxide which are highly caustic materials.

The potassium oxide and potassium hydroxide solids present problems similar to those created by the sodium oxide and sodium hydroxide combustion products from sodium azide based gas generant compositions. For instance, sodium azide-based gas generants have combustion products that can be toxic because molybdenum disulfide and sulfur are presently the preferred oxidizers for use with sodium azide. The reaction of these materials with sodiumazide produces toxic hydrogen sulfide gas, corrosive sodium oxide, sodium sulfide, and sodium hydroxide powder. Rescue workers and automobile occupants have complained about both the hydrogen sulfide gas and the corrosive powder, e.g., sodium hydroxide, produced by the operation of sodium azide-based gas generants. Like problems are to be expected with the potassium by-products from a non-azide gas generant based on the potassium salt of 5-nitrobarbituric acid.

It would, therefore, be a significant advance in the art to provide a non-azide fueled gas generant composition which does not suffer from the defects associated with the presently proposed sodium azide fueled gas generants and the aforementioned composition composed of a restricted class of metallic salts of 5-nitrobarbituric acid and a restricted class of oxidizers.

Such compositions are disclosed and claimed herein.

SUMMARY AND OBJECTS OF THE INVENTION

A non-azide gas generating composition according to the present invention comprises a fuel effective amount of at least one non-metallic salt of 5-nitrobarbituric acid and an oxidizing effective amount of an inorganic oxidizer selected from among nitrate, nitrite, peroxide, metal oxide, metal hydroxide, perchlorate, and chlorate oxidizers as well as mixtures thereof.

The non-metallic fuel in the present composition mitigates, if not avoids, the problems with the combustion by-products produced by the metal salts of 5-nitrobarbituric acid and by the conventional sodiumazide fueled gas generants.

The present non-metallic fueled composition can combust at a sufficiently rapid rate to generate satisfactory quantities of non-toxic gases. The amount of gas generation compares favorably to a baseline composition which is fueled by the potassium salt of 5-nitrobarbituric acid. The gases generated by the present composition are suitable for use in deploying and inflating supplemental restraint systems, such as air bags and the like.

DETAILED DESCRIPTION OF THE INVENTION

A non-azide gas generating composition according to the present invention comprises a fuel effective amount of at least one non-metallic salt of 5-nitrobarbituric acid and an oxidizing effective amount of an oxidizer selected from among inorganic nitrates, inorganic nitrites, metal oxides, metal hydroxides, inorganic perchlorates, inorganic chlorates, inorganic peroxides, and mixtures thereof.

A composition according to the present invention comprises about 15 to about 60% by weight, advantageously about 22 to about 45% by weight, of at least one heterocyclic compound represented by the formula (I):

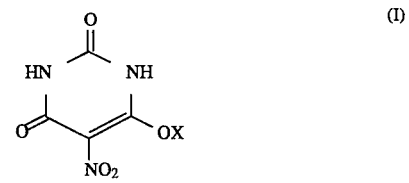

wherein X is a non-metallic cation, and about 40% to about 85% by weight, preferably about 55% to about 78% by weight, of an inorganic oxidizer selected from among nitrite oxidizers, metal peroxides, nitrate oxidizers, metal oxides, metal hydroxides, perchlorate oxidizers, chlorate oxidizers, and mixtures thereof.

In a preferred embodiment, the relative amounts of the organic salt of 5-nitrobarbituric acid and the oxidizer are in such a ratio that combusting the composition can overwhelmingly produce carbon dioxide, water and nitrogen, and minimal amounts of carbon monoxide, $NO_x$ and oxygen as shown in, for instance, Examples 6 and 7.

The non-metallic cation can be selected, for instance, from among organic cations and, in principle, cations of non-carbon heterocycles such as borazines Thus, the cation X can be a non-metallic cation of a high nitrogen-content base. Exemplary non-metallic cations include, among others, ammonium, hydrazinium, guanidinium, aminoguanidinium, diaminoguanidinium, triaminoguanidinium, biguanidinium, aminotriazolium, guanizinium, aminotetrazolium, and hydrazino tetrazolium. Other non-metallic salts of 5-nitrobarbituric acid and their preparation are described in J. Am. Chem. Soc., 62:590 (1940), the complete disclosure of which is incorporated herein by reference.

The oxidizer is a metal peroxide, an inorganic nitrate, an inorganic nitrite, a metal oxide, a metal hydroxide, an inorganic chlorate, an inorganic perchlorate, or a mixture thereof. Thus, suitable oxidizers include a metal nitrate, a metal nitrite, a metal chlorate, a metal perchlorate, a metal peroxide, ammonium nitrate, ammonium perchlorate and the like. Suitable oxidizing compounds can have a cation such as, for instance, ammonium, metal ions of metals from Group 1-A of the Periodic Table, as well as metal ions of barium, bismuth, calcium, cobalt, copper, iron, manganese, molybdenum, strontium, tin, tungsten and, for instance, zinc. By preference, the oxidizer is free of cations of alkali metals, such as sodium or potassium, when the present composition is used as the gas generant in a supplemental safety restraint system. The oxides and hydroxides of metals, such as bismuth, copper, cobalt, iron, magnesium, manganese, molybdenum, and tungsten, such as CuO, $Co_2O_3$, $Fe_2O_3$, $MnO_2$, $MoO_3$, $Bi_2MoO_6$, $Bi_2O_3$, and $Cu(OH)_2$, can be used. Other exemplary oxidizers include, among others, metal peroxides or nitrates or nitrites of, for instance, sodium, potassium, magnesium, strontium, copper, cobalt, chromium or zinc. The oxide and hydroxide oxidizing agents mentioned above can, if desired, be combined with other oxidizers such as, for instance, $Sr(NO_3)_2$, $NH_4ClO_4$ and $KNO_3$, for a particular application, such as to provide increased flame temperature or to modify the gas product yields.

The method by which the non-metallic salts of 5-nitrobarbituric acid are prepared is not critical. Various salts of 5-nitrobarbituric acid and their preparation are described in *J. Am. Chem. Soc.*, 62:590 (1940). Methods for making 5-nitrobarbituric acid from which the salts can be prepared are known, and include those described in *Organic Synthesis*, Coll. Vol. II, pages 440–41 the complete disclosure of which is incorporated herein by reference.

Salts of 5-nitrobarbituric acid can also be prepared by allowing a compound having the formula (II)

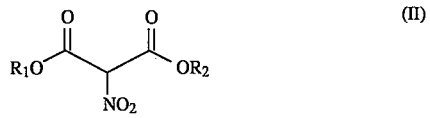

(II)

wherein $R_1$ and $R_2$ are the same or different and are alkyl or substituted alkyl, to react with an effective amount of urea to obtain 5-nitrobarbituric acid. Salts are obtained by treating the reaction product, 5-nitrobarbituric acid, with an effective amount of a compound, such as an organic base or another cation source, MX, in order to form the desired salt, which treatment can, if desired, be conducted in situ without prior isolation of the acid. If desired, a compound according to formula (II) can be prepared in situ, such as by the direct nitration of cyanoacetic acid, by adapting the procedures described in, for instance, *Gazzeta Chimica Iraliana*, 42:223, the complete disclosure of which is incorporated herein by reference. A compound according to formula (II) can also be obtained by nitrating the corresponding compound. For example, a dialkyl malonate, such as diethyl malonate, can be nitrated to obtain a compound represented by formula (II). Suitable nitrating reagents include, among others, nitric acid, acetic acid or acetic anhydride with ammonium nitrate, acetic acid or acetic anhydride with one or more metal nitrates such as $Mn(NO_3)_2$ or $Cu(NO_3)_2$.

Additives conventionally used in gas generating compositions, propellants, and explosives, such as binders, burn rate modifiers, slag formers, release agents, and additives which effectively remove $NO_x$ can, if desired, be included in the compositions according to the present invention. Typical binders include lactose, boric acid, silicates including magnesium silicate, polypropylene carbonate, polyethylene glycol, and other conventional polymeric binders. Typical burn rate modifiers include $Fe_2O_3$, $K_2B_{12}H_{12}$, $Bi_2MoO_6$, and graphite carbon fibers. A number of slag forming agents are known and include, for example, clays, talcs, silicon oxides, alkaline earth oxides, hydroxides, oxalates, of which magnesium carbonate, and magnesium hydroxide are exemplary. A number of additives and/or agents are also known to reduce or eliminate the oxides of nitrogen from the combustion products of a gas generant composition, including alkali metal salts and complexes of tetrazoles, aminotetrazoles, triazoles and related nitrogen heterocycles of which potassium aminotetrazole, sodium carbonate and potassium carbonate are exemplary. The composition can also include materials which facilitate the release of the composition from a mold such as graphite, molybdenum sulfide, calcium stearate, or boron nitride.

The compositions of the present invention can be formed into the desired shape, such as pellets, by conventional means. Pellets are the presently preferred form for use in supplemental safety restraint systems such as air bags.

The present gas generant compositions can be combusted to give good gas yields of acceptable gas products. Several of the more preferred compositions have a low flame temperature. Solids produced during combustion do not suffer problems noted earlier with respect to sodium azide and the potassium salt of dilituric acid. Therefore, a method for generating gas comprises igniting the composition according to the present invention.

The present invention also contemplates a vehicle having an inflatable restraining device, such as an automobile air bag system, which comprises a collapsed, inflatable air bag, a means for generating gas connected to that air bag for inflating the air bag wherein the gas generating means includes an igniter and also contains a nontoxic gas generating composition which comprises a fuel and an oxidizer therefore wherein the fuel comprises a composition according to the present invention. Suitable means for generating gas include gas generating devices which are used in supplemental safety restraint systems used in the automotive industry. The supplemental safety restraint system may, if desired, include conventional screen packs to remove particulates, if any, formed while the gas generant is combusted.

The compositions of the present invention are easily ignited with conventional igniters. Igniters using materials such as boron/potassium nitrate are usable with the compositions of the present invention.

As demonstrated in Examples 8 and 9, the compositions of the present invention are readily adapted for use with conventional hybrid air bag inflator technology. Hybrid inflator technology is based on heating a stored inert gas (argon or helium) to a desired temperature by burning a small amount of propellant. Hybrid inflators do not require cooling filters used with pyrotechnic inflators to cool combustion gases, because hybrid inflators are able to provide a lower temperature gas. The gas discharge temperature can be selectively changed by adjusting the ratio of inert gas weight to propellant weight. The higher the gas weight to propellant weight ratio, the cooler the gas discharge temperature for a given propellent formulation.

Therefore, the present invention also contemplates a vehicle having a hybrid gas generating system which comprises a pressure tank having a rupturable opening, a predetermined amount of inert gas disposed within that pressure tank; a gas generating device for producing hot combustion gases and having means for rupturing the rupturable opening; and means for igniting the gas generating composition. The tank has a rupturable opening which can be broken by a piston when the gas generating device is ignited. The gas generating device is configured and positioned relative to the pressure tank so that hot combustion gases are mixed with and heat the inert gas. Suitable inert gases include, among others, argon, and helium and mixtures thereof. The mixed and heated gases exit the pressure tank through the opening and ultimately exit the hybrid inflator and deploy an inflatable bag or balloon, such as an automobile air bag. The gas generating device contains a composition according to the present invention.

The present inventions are described further in the following non-limiting examples.

chamber includes a fluid outlet to allow hot gas to heat and expand the argon gas to fill a 60 liter tank. The test fixture is configured to approximate the environment of a hybrid system (automobile air bag).

TABLE I

|  | Example 1 | Example 2 | Example 3 | Example 4 | Example 5 | Example 6 | Example 7 | Example 8 (hybrid) | Example 9 (hybrid) | Example 10 |
|---|---|---|---|---|---|---|---|---|---|---|
| ammonium DL |  |  |  |  |  |  | 42.81 |  |  |  |
| hydrazinium DL |  |  |  |  |  |  |  |  |  | 42.71 |
| triaminoguanyl DL | 38.41 | 24.8 | 24.92 |  |  |  |  | 4.52 |  |  |
| guanyl DL |  |  |  | 37.87 | 24.37 | 24.49 |  |  | 2.29 |  |
| strontium nitrate | 61.59 |  |  | 62.13 |  |  | 57.19 | 7.24 |  | 57.29 |
| ammonium nitrate |  | 75.2 |  |  | 75.63 |  |  |  | 7.09 |  |
| copper oxide |  |  | 75.08 |  |  | 75.51 |  |  |  |  |
| argon |  |  |  |  |  |  |  | 88.24 | 90.62 |  |
| gas yield (rel to SOTA) | 1.38 | 1.9 | 1.28 | 1.29 | 1.86 | 1.18 | 1.35 |  |  | 1.38 |
| flame temperature (°K.) | 2315 | 2240 | 1358 | 2011 | 2107 | 1005 | 1936 | 927 | 780 | 2113 |
| ppm CO | 7500 | 2440 | 68 | 2047 | 1480 | 0 | 1397 | 0 | 0 | 3436 |
| % CO2 | 28.43 | 10.5 | 33.33 | 36 | 12.65 | 41.67 | 39.06 | 1.93 | 1.86 | 35.01 |
| ppm H2 | 1507 | 2450 | 34 | 362 | 1340 | 0 | 246 | 0 | 0 | 614 |
| ppm NO | 1495 | 830 | 0 | 373 | 460 | 0 | 235 | 0 | 0 | 614 |
| % H2O | 31.74 | 56.5 | 36.66 | 28.89 | 56.15 | 33.33 | 29.35 | 3.65 | 8.16 | 30.8 |
| % N2 | 38.44 | 32.1 | 30 | 34.74 | 30.7 | 25 | 31.34 | 4.41 | 4.46 | 33.56 |
| ppm O2 | 3328 | 1660 | 0 | 927 | 0.10% | 0 | 648 | 0 | 0 | 1561 |
| % argon | 0 | 0 | 0 | 0 | 0 | 0 | 0 | 90.04 | 85.52 | 0 |
| mass % gases | 69.79 | 100 | 40.02 | 69.57 | 100 | 39.68 | 72 | 95 | 100 | 82 |

EXAMPLES

Various compositions were prepared to illustrate the advantages of the present invention.

Table I summarizes both the compositions and the data concerning their combustion. In Table I, SOTA designates a baseline conventional sodium azide gas generant (sodium azide, $Fe_2O_3$, $KNO_3$, and molybdenum disulfide).

Unless otherwise stated, the salts of 5-nitrobarbituric acid are prepared by neutralizing 5-nitrobarbituric acid with an organic base according to the conventional synthesis as reported in literature.

The actual gas generant compositions are formulated and pressed into pellets. In Examples 1 through 7 and 10, the formulations are tested by combusting a multiple pellet charge in a ballistic test device. The test device comprises a combustion chamber equipped with a conventional 0.25 gram $BKNO_3$ igniter. The combustion chamber includes a fluid outlet to a 13 liter tank. The test fixture is configured to approximate the environment of an automobile air bag.

In Examples 8 and 9, the formulations are tested by combusting a multiple pellet charge in a ballistic test device simulating a hybrid gas generating system having a predetermined amount of argon as the inert gas. The test device is equipped with a combustion chamber equipped with a conventional 1.0 gram $BKNO_3$ igniter. The combustion The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A composition comprising:
   (a) about 15 to about 60 % by weight of at least one heterocyclic compound represented by the formula:

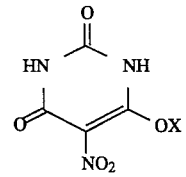

wherein X is a non-metallic cation; and (b) about 85% to about 40% by weight of at least one oxidizer selected from the group consisting of inorganic nitrites, inorganic nitrates, metal oxides, metal hydroxides, metal peroxides, inorganic chlorates, inorganic perchlorates, and mixtures thereof.

2. A composition according to claim 1, wherein X is selected from the group consisting of organic cations and cations of non-carbon heterocycles.

3. A composition according to claim 2 wherein X is a cation of a high nitrogen-content base.

4. A composition according to claim 1, wherein X is selected from the group consisting of ammonium, hydrazinium, guanidinium, aminoguanidinium, diaminoguanidinium, triaminoguanidinium, biguanidinium, aminotriazolium, guanizinium, aminotetrazolium, and hydrazino tetrazolium.

5. A composition according to claim 4, wherein X is selected from the group consisting of guanyl and ammonium.

6. A composition according to claim 1, wherein the oxidizer is a compound having a cation selected from the group consisting of ammonium, a metal from Group I-A of the Periodic Table, barium, bismuth, calcium, cobalt, copper, iron, magnesium, manganese, molybdenum, strontium, tin, tungsten and zinc.

7. A composition according to claim 1, wherein the oxidizer does not contain a cation of a metal from Group I-A of the Periodic Table.

8. A composition according to claim 1, wherein said oxidizer is selected from the group consisting of a metal nitrate, a metal oxide and mixtures thereof.

9. A composition according to claim 8, wherein said oxidizer is selected from the group consisting of CuO, $Co_2O_3$, $Fe_2O_3$, $MoO_3$, $Bi_2MoO_6$, $Bi_2O_3$, $Cu(OH)_2$, $Sr(NO_3)_2$, and mixtures thereof.

10. A composition according to claim 1, wherein said oxidizer is selected from the group consisting of ammonium nitrate, strontium nitrate, copper oxide and mixtures thereof.

11. A composition according to claim 1, wherein said salt of 5-nitrobarbituric acid is present in an amount of about 22 to about 45% by weight.

12. A composition according to claim 1, wherein X is selected from the group consisting of ammonium, hydrazinium, guanidinium, aminoguanidinium, diaminoguanidinium, triaminoguanidinium, biguanidinium, aminotriazolium, guanizinium, aminotetrazolium, and hydrazino tetrazolium; and the oxidizer is a salt having a cation selected from the group consisting of ammonium, a metal from Group I-A of the Periodic Table, barium, bismuth, calcium, cobalt, copper, iron, magnesium, manganese, molybdenum, strontium, tin, tungsten, and zinc.

13. A composition according to claim 12, wherein said oxidizer is a metal nitrate or metal oxide.

14. A method for generating gas which comprises igniting the composition according to claim 1.

15. A composition comprising a fuel effective amount of at least one heterocyclic compound represented by the formula:

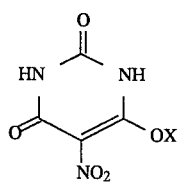

wherein X is a non-metallic cation; and an oxidizing effective amount of at least one oxidizer selected from the group consisting of inorganic nitrites, inorganic nitrates, metal oxides, metal hydroxides, metal peroxides, inorganic chlorates, and inorganic perchlorates.

16. A hybrid gas-generating system comprising:

a pressure tank having a rupturable opening, said pressure tank containing an inert gas;

a gas-generating device for producing hot combustion gases and for rupturing said rupturable opening, said gas-generating device being configured in relation to said pressure tank such that hot combustion gases are mixed with and heat said inert gas, said gas-generating device containing a gas-generating composition comprising (a) a fuel effective amount of at least one heterocyclic compound represented by the formula:

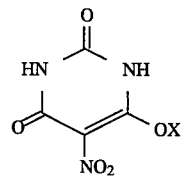

wherein X is a non-metallic cation; and (b) an effective oxidizing amount of at least one oxidizer selected from the group consisting of inorganic nitrites, inorganic nitrates, metal oxides, metal hydroxides, metal peroxides, inorganic perchlorates, and inorganic chlorates; and means for igniting said gas-generating composition.

17. A hybrid gas-generating system according to claim 16, wherein said inert gas is argon or helium.

18. An automobile air bag system comprising a collapsed, inflatable air bag; and a gas generating device connected to said air bag for inflating said air bag, said gas generating device containing a gas generating composition comprising a fuel and an oxidizer therefor, wherein said fuel is a fuel effective amount of at least one heterocyclic compound represented by the forumla:

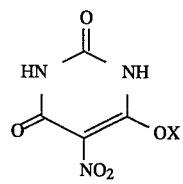

wherein X is a non-metallic cation; and an oxidizing effective amount of at least one oxidizer selected from the group consisting of inorganic nitrites, inorganic nitrates, metal oxides, metal hydroxides, metal peroxides, inorganic perchlorates, and inorganic chlorates.

* * * * *